(12) United States Patent
Ravo

(10) Patent No.: US 7,771,384 B2
(45) Date of Patent: Aug. 10, 2010

(54) TROCAR WITH INTEGRAL IRRIGATION AND SUCTION TUBE

(76) Inventor: Biagio Ravo, Rome America Hospital, Via Emilio Longoni, 69, Rome (IT) 00155

( * ) Notice: Subject to any disclaimer, the term of this patent is extended or adjusted under 35 U.S.C. 154(b) by 595 days.

(21) Appl. No.: 10/922,548

(22) Filed: Aug. 20, 2004

(65) Prior Publication Data

US 2005/0043683 A1    Feb. 24, 2005

Related U.S. Application Data

(60) Provisional application No. 60/496,384, filed on Aug. 20, 2003.

(51) Int. Cl.
*A61M 1/00* (2006.01)
(52) U.S. Cl. .............. 604/35; 604/19; 604/27
(58) Field of Classification Search ........... 604/19, 604/27–28, 35, 93.01, 164.01, 164.12, 167.01, 604/167.03, 181, 182, 239, 246, 264, 240, 604/272, 158; 606/108; 600/114, 121, 123, 600/156–159
See application file for complete search history.

(56) References Cited

U.S. PATENT DOCUMENTS

| | | | |
|---|---|---|---|
| 4,207,874 A | | 6/1980 | Choy |
| 4,617,013 A | | 10/1986 | Betz |
| 4,708,136 A | | 11/1987 | Saito |
| 5,201,908 A | * | 4/1993 | Jones .................. 600/123 |
| 5,279,551 A | * | 1/1994 | James .................. 604/44 |
| 5,792,122 A | * | 8/1998 | Brimhall et al. ............. 604/263 |
| 5,830,231 A | * | 11/1998 | Geiges, Jr. .................. 606/205 |
| 6,592,567 B1 | * | 7/2003 | Levin et al. .................. 604/509 |
| 6,699,185 B2 | * | 3/2004 | Gminder et al. ............. 600/157 |
| 2004/0087831 A1 | * | 5/2004 | Michels et al. ............. 600/114 |

* cited by examiner

*Primary Examiner*—Nicholas D Lucchesi
*Assistant Examiner*—Laura A Bouchelle
(74) *Attorney, Agent, or Firm*—24IP Law Group; Timothy R. DeWitt

(57) ABSTRACT

A trocar tube incorporating integral irrigation and aspiration capabilities with positioning control. These capabilities can be used in conjunction with endoscopic tools which can be fed through the trocar housing. Specifically, the invention can be used to clean the lens of a laparoscope while it is in place in the trocar tube to eliminate the need for removal of the laparoscope for cleansing. The trocar tube telescoping tip permits independent control of the position of irrigation and aspiration while other tools are in use. Trocar tube channels in the wall of the trocar tube enable fluids to be fed to the distal end of the trocar tube, and enable material to be aspirated from the distal end of the trocar tube. The trocar tube channels are connected to a fluid source and an aspirating device. Aspiration and fluid flow are controlled by a foot pedal or other device that allows hands-free control. The specific improvements in endoscopic procedures afforded by this device inhere in the ability to leave irrigation and aspiration capabilities in place throughout an endoscopic procedure, the ability to supply irrigation and aspiration capabilities to various types of endoscopic tools, including existing laparoscopic tools without self-cleaning capabilities, the ability to direct irrigation and aspiration flow, the minimization of the need to place and remove multi-purpose tools during the procedure.

4 Claims, 3 Drawing Sheets

TROCAR WITH INTEGRAL IRRIGATION AND SUCTION TUBE

CROSS-REFERENCE TO RELATED APPLICATIONS

This application claims the benefit of U.S. Provisional Application Ser. No. 60/496,384 filed on Aug. 20, 2003 by inventor Biagio Ravo.

STATEMENT REGARDING FEDERALLY SPONSORED RESEARCH OR DEVELOPMENT

None

FIELD OF THE INVENTION

The present invention relates to a trocar tube with irrigation and suction capabilities, and directional control of these capabilities, for use with a variety of endoscopic instruments.

BACKGROUND OF THE INVENTION

A trocar is a surgical instrument, contained in a sheath that is used for making a bodily incision. In typical procedures, the inner portion of the trocar is removed from the incision and the surrounding sheath is left in place so that surgical tools may be inserted into the incision. A laparoscope, which is one class of an endoscope, is an example of such a tool. Typically, a laparoscope includes a rigid elongated sheath tube which encloses a image transferring means channel which receives a fiber optic image light bundle or relay lens system. The image transferring means channel is typically surrounded by fiber optic light carrying means. The distal end of the laparoscope is used to develop an optical image of an operating site within a cavity and the operating site is illuminated by light which is carried to the operating site by the fiber optic light carrying means. The optical image is transmitted through the image transferring means to the proximal end of the laparoscope where a viewable image is observed by the surgeon. The state-of-the-art laparoscopes are usually inserted through a cannula and trocar assembly which makes an incision or opening in the navel or belly-button of a patient. The purpose of making the incision in the navel or belly-button is to minimize the appearance of the surgical scar which remains upon completion of the surgical procedure. It is also known in the act to utilize a primary cannula and trocar assembly to form the initial opening through the navel or belly-button into the abdomen or the peritoneal cavity and use smaller cannula and trocar assemblies which are inserted into other smaller incisions to provide access to the peritoneal cavity for passing working tools. In the known laparoscopic procedures, the peritoneal cavity is insufflated with an appropriate fluid (gas) such as carbon dioxide ($CO_2$) gas, concomitant with laparoscopic or peritoneoscopic examination, diagnosis and/or treatment, including the excision of structure and tissues in the peritoneal cavity. In the recent past, the type of surgeries performed using laparoscopic procedures has been expanded into new minimum invasive surgical procedures. One such new procedure utilizes the laparoscope, with other appropriate instruments, for performing laparoscopic cholecystectomy which is essentially a minimum invasive surgical method for removal of a gallbladder. Similar minimum invasive surgical techniques are being developed using laparoscopes to remove other organs, such as the appendix, kidney or tissues, such as from the liver, also located in the peritoneal cavity (etc.).

It is also known in the art that when utilizing a laparoscope in a laparoscopic procedure, such as, for example, the laparoscopic cholecystectomy briefly described above, it is necessary that the distal lens be free from light impeding agents such as a layer of fog, protein material or organic material. It is the desire of the surgeon to keep the laparoscope in the peritoneal cavity at all times.

However, it is known that when the distal tip of the laparoscope is inserted into the peritoneal cavity, a fogging occurs across the distal tip which impedes the passage of the optical image and which interferes with the ability of the surgeon to view the operating site. This fogging condition is due to the fact that the operating room temperature is in the order of 20 degrees C. (68 degrees F.). However, the interior of the peritoneal cavity or abdomen is generally at blood temperature which is typically in the order of 37 degrees C. (98.6 degrees F.). Thus, when a laparoscope, which is maintained at room temperature in the operating room which is typically 20 degrees C. has the distal tip thereof at room temperature of about 20 degrees C. inserted into the abdomen having a temperature of approximately 37 degrees C., the temperature differential therebetween is sufficient to cause instant fogging of the distal lens.

Once known method for solving this problem is to heat the distal tip of the laparoscope by a variety of means. One method that is utilized to heat the distal tip is to insert the distal tip into a container of hot water to raise the temperature of the distal tip to approximately 37 degrees C. Another known technique is to place the distal tip in hot towels to raise the temperature thereof to approximately 37 degrees C.

In addition to the above fogging problem, other image impeding programs are encountered during a procedure. When a surgeon is performing a procedure, that procedure normally results in particulate matter such as protein, blood, tissue and the like, begin splattered through the operating site during the procedure. Typically, certain of the particulate matter will adhere to the distal surface and transparent member located at the distal tip of the laparoscope thereby impeding the transmission or passage of the optical image through the transparent member. This is particularly true during use of laser and electroncautery procedures for removing tissue.

In a typical laparoscopic procedure, particulate matter accumulates on the distal end three or four times during a procedure. Each time the optical image is impeded by the accumulation of particulate matter, it is necessary for the surgeon to remove the laparoscope through the cannula and trocar assembly, to physically wipe the particulate matter off of the transparent member, located at the distal tip of the laparoscope, and then reinsert the laparoscope through the cannula and trocar assembly back into the abdominal or peritoneal cavity to continue the procedure. For this reason, a method of removing particulate matter from a laparoscope, or other endoscopic tool, while it remains in place is desirable.

Tools having suction and irrigation features are known in the art for endoscopic applications. Recently, combined suction-irrigation tools with additional features have been developed. U.S. Pat. No. 4,617,013 to Betz discloses a "Method and Apparatus For Surgical Irrigation, Aspiration and Illumination" having coaxial fiber optic, aspiration an irrigation tubes. The fiber optic is used for providing lighting. No laparoscope is present in the device; therefore, the suction and irrigation features do not clean a laparoscope housed within. U.S. Pat. No. 4,207.874 to Choy discloses a "Laser Tunneling Device" which is a probe for a tube such as a blood vessel. The probe includes central fiber optics for illumination, viewing and laser output surrounded by a coaxial tube with a switchable valve for aspiration or irrigation. The irrigating fluid is a dye used to locate an obstruction, and suction is used to remove vaporized debris produced by laser action on an obstruction.

While many of the tools of the prior art served a purpose that the time they were invented, they are generally inapplicable in today's modem endoscopic surgical procedures. An endoscopic procedure typically involves the use of trocars for making one or more small incisions in the abdomen or chest cavity. Trocar tubes are then left in place in the abdomen or chest cavity so that optical tools may be inserted therethrough for viewing and endoscopic surgical tools may be inserted therethrough for operating. A camera or magnifying lens optical tool is often inserted through the largest diameter trocar tube (e.g. 10 mm diameter) while a cutter, dissector, or other surgical instrument is inserted through a similarly sized or small diameter trocar tube (e.g. 5 mm diameter) or purposes of manipulating and/or cutting the internal organ. Sometimes it is desirable to have several trocar tubes in place at once in order to receive several surgical instruments. In this matter, organ or tissue may be grasped with one surgical instrument, and simultaneously may be cut or stitched with another surgical instrument; all under view of the surgeon via the camera in place in another trocar tube.

Those skilled in the art will appreciate that endoscopy is a rapidly growing field of surgery because it is less invasive than classical surgery. However, it will also be appreciated that even with endoscopic surgery where the incisions are typically small, it is advantageous to limit the number of incisions made. The number of incisions must be balanced against the desirability of having several tools inserted and available simultaneously to the surgeon. Likewise, while it is possible to remove endoscopic tools and insert different tools during a procedure, it will be appreciated that repeated insertion and removal of different endoscopic tools through the trocar tubes is preferably avoided, as it can be difficult to locate the new tool at a desire location, and each insertion of a tool increases the risk of unnecessary trauma to the surgical site area.

Some attempts have been made to provide multi-functional endoscopic tools so that the number of incisions may be minimized while at the same time providing the physician with several tools available simultaneously. For example, U.S. Pat. No. 4,708,136 to Saito discloses a "Cautery Hemostatic Unit" which is deliverable through an endoscope and includes an irrigation nozzle. Other combination endoscopic tools are known and generally include combination suction-irrigation and suction-cautery probes. All of these probes occupy a trocar tube when in use and no other tool may be inserted in the trocar when occupied by one of these probes. Additional combinational tools and prototypes recently introduced include tools which have a plurality of different distal end portions which can be attached and removed from a single handle as desired to accomplish different functions. However, this arrangement requires repeated insertion and removal of the endoscopic tool through the trocar tube to the surgical area.

Accordingly, there remains a need for a device by which a combination suction-irrigation capability can be supplied to endoscopic tools, particularly to laparoscopic devices. Because it is desirable to minimize the placement and removal of endoscopic tools, it is advantageous to incorporate irrigation and aspiration capabilities in a device that will remain in place throughout an endoscopic procedure, to insert and remove the simplest, smallest devices possible, and to provide directional control for irrigation and aspiration capabilities so that they may be used with a variety of laparoscopic tools.

SUMMARY OF THE INVENTION

The present invention is a trocar tube incorporating integral irrigation and aspiration capabilities with positioning control. These capabilities can be used in conjunction with endoscopic tools which can be fed through the trocar housing. Specifically, the invention can be used to clean the lens of a laparoscope while it is in place in the trocar tube to eliminate the need for removal of the laparoscope for cleansing. The trocar tube telescoping tip permits independent control of the position of irrigation and aspiration while other tools are in use. Trocar tube channels in the wall of the trocar tube enable fluids to be fed to the distal end of the trocar tube. The trocar tube channels are connected to a fluid source and an aspirating device. Aspiration and fluid flow are controlled by a foot pedal or other device that allows hands-free control. The specific improvements in endoscopic procedures afforded by this device inhere in the ability to leave irrigation and aspiration capabilities in place throughout an endoscopic procedure, the ability to supply irrigation and aspiration capabilities to various types of endoscopic tools, including existing laparoscopic tools without self-cleaning capabilities, the ability to direct irrigation and aspiration flow, and the minimization of the need to place and remove multi-purpose tools during the procedure.

Still other aspects, features, and advantages of the present invention are readily apparent from the following detailed description, simply by illustrating preferable embodiments and implementations. The present invention is also capable of other and different embodiments, and its several details can be modified in various respects, all without departing from the spirit and scope of the present invention. Accordingly, the drawings and descriptions are to be regarded as illustration in nature, and not as restrictive.

BRIEF DESCRIPTION OF THE DRAWINGS

The accompanying drawings, which are incorporated in and constitute a part of this specification illustrate some embodiments of the invention and, together with the description, serve to explain the objects, advantages, and principles of the invention. To facilitate the description, the preferred embodiment of the invention will be referred to herein as the "integrated identification and verification station". In the drawings.

DETAILED DESCRIPTION OF THE INVENTION

Figure 1:
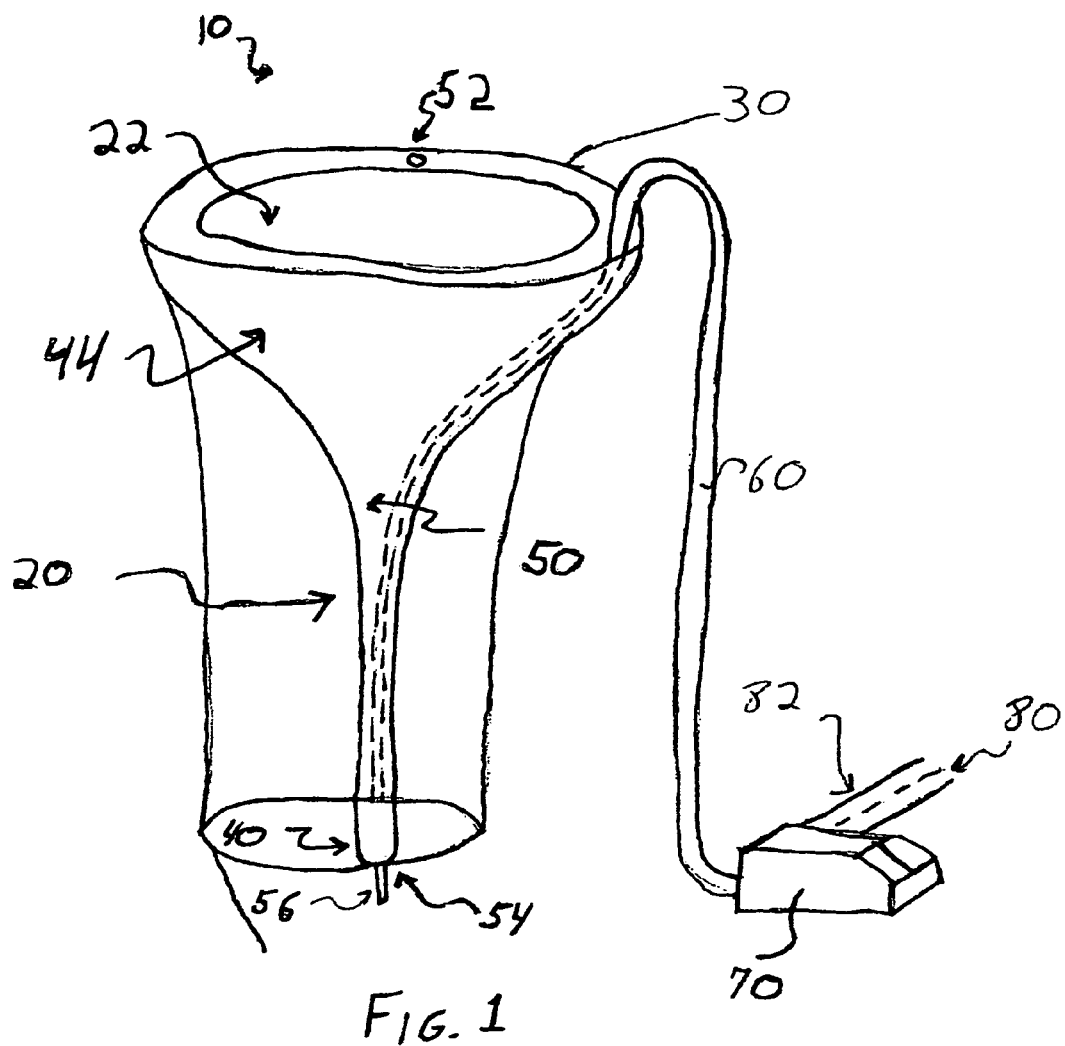
FIG. 1 is a schematic representation of the trocar tube, including irrigation and aspiration control components.

The present invention is a trocar tube incorporating integral irrigation and aspiration capabilities with positioning control. The tube contains an enlarged proximal end to facilitate insertion of endoscopic tools and instruments. The tube is constructed of a flexible material and is adapted for insertion into incisions made for surgical procedures. Trocar tube channels, incorporated into the wall of the trocar tube, enable irrigation and aspiration capabilities to be supplied to the distal end of the trocar tube. Irrigation involves the supply of fluid for purposes such as cleansing; aspiration is the removal or [sic]

fluids or particles through suction. For particular applications, the trocar tubing may be sterilized and packaged in sterile packaging prior to use. FIG. 1 illustrates the function of the trocar tube assembly 10 as used in an endoscopic procedure.

An endoscopic procedure typically involves the use of the trocars for making one or more small incisions in the abdomen or chest cavity. Trocar tubes are then left in place in the abdomen or chest cavity so that optical tools may be inserted therethrough for viewing and endoscopic surgical tools may be inserted therethrough for operating. A camera or magnifying lens optical tool is often inserted through the largest diameter trocar tube (e.g., 10 mm diameter) while a cutter, dissector, cauterizer or other surgical instrument is inserted through a similarly sized or smaller diameter trocar tube (e.g., 5 mm diameter) for purposes of manipulating and/or cutting the internal organ. Sometimes it is desirable to have several trocar tubes in place at once in order to receive several surgical instruments. In this manner, organ or tissue may be grasped with one surgical instrument, and simultaneously may be cut or stitched with another surgical instrument; all under the view of the surgeon via the camera in place in another trocar tube.

Trocar tube 20 is employed in an endoscopic procedure so that endoscopic instruments and tools can be inserted into trocar tube passage 22 at a trocar tube proximal end 30 and fed through the trocar tube 20 to a trocar tube distal end 40. The flexible wall 44 of trocar tube 20 contains at least one trocar tube channel 50 disposed axially to the body of trocar tube 20, each trocar tube channel having a trocar tube channel proximal end 52 and a trocar tube channel distal end 54. A trocar tube channel telescoping tip 56 is attached to, and is in fluid communication with, a trocar tube channel 50 at trocar tube channel distal end 54. Trocar tube channel 50 is configured to accommodate irrigation and aspiration capabilities. The position of irrigation and aspiration can be directed through the positioning of trocar tube channel telescoping tip 56.

Irrigation and aspiration are supplied to the trocar tube through one or more trocar tube channel connecting tubes 60, in fluid communication with one or more trocar tube channels 50 at one end and to a control valve 70 at the other end. Control valve 70 is preferably a foot or knee pedal or other type of control allowing hands-free control of irrigation and aspiration. Control valve 70 is in fluid communication with an irrigation feed 80 and an aspiration feed 82. Irrigation may be used in conjunction with electrosurgery, other surgical procedures or to clean the lens of a laparoscopic device.

Figure 2:
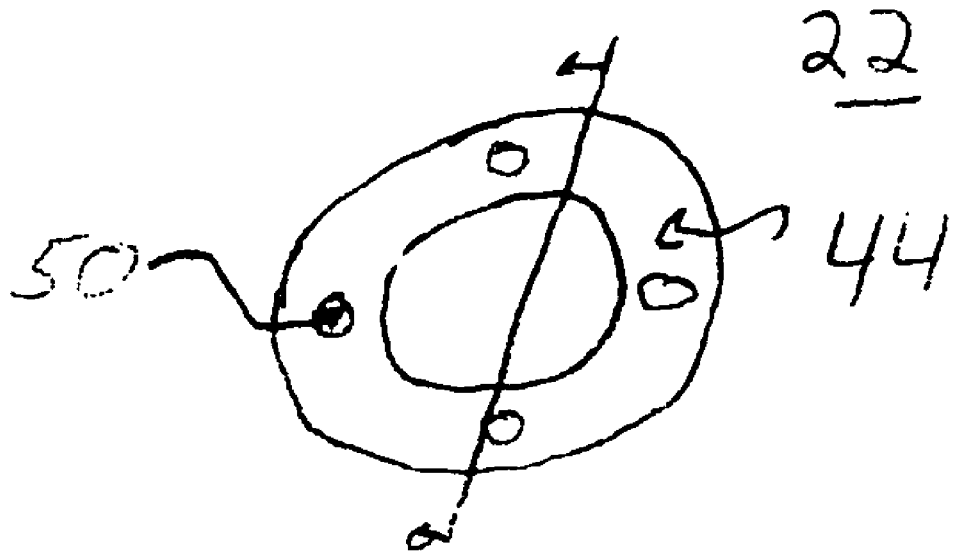
FIG. 2 is a cross-section representation of one embodiment of the trocar tube.

FIG. 2 illustrates a cross-section of one embodiment of trocar tube 20. In this embodiment, four trocar tube channels 50 are incorporated into the wall of trocar tube 20. The circular geometry of the exterior of trocar tube 20 is maintained to facilitate the placement and the removal of the trocar tube.

Figure 3:
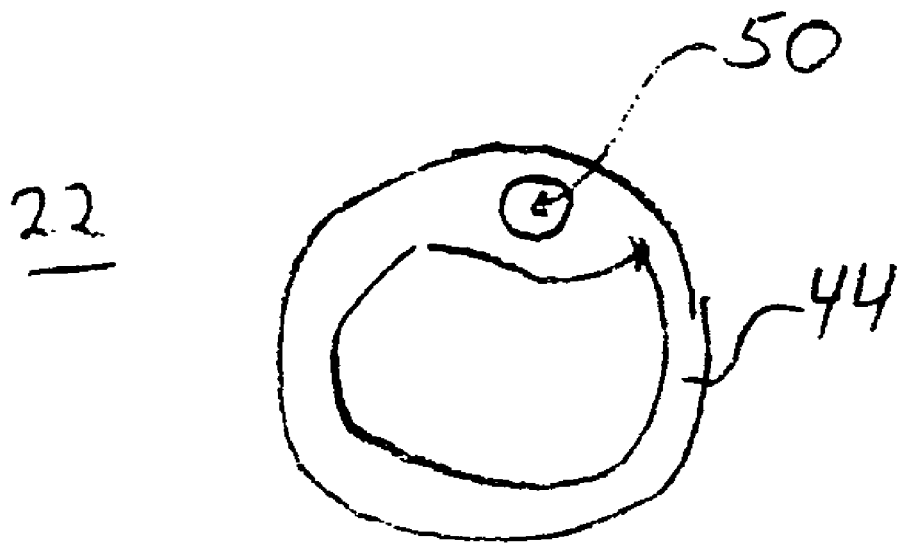
FIG. 3 is a cross-section representation of another embodiment of the trocar tube.

FIG. 3 illustrates a cross-section of another embodiment of trocar tube 20. In this embodiment, one trocar tube channel 50 is incorporated into the wall of trocar tube 20. The circular geometry of the exterior of trocar tube 20 is maintained to facilitate the placement and the removal of the trocar tube.

Figure 4:
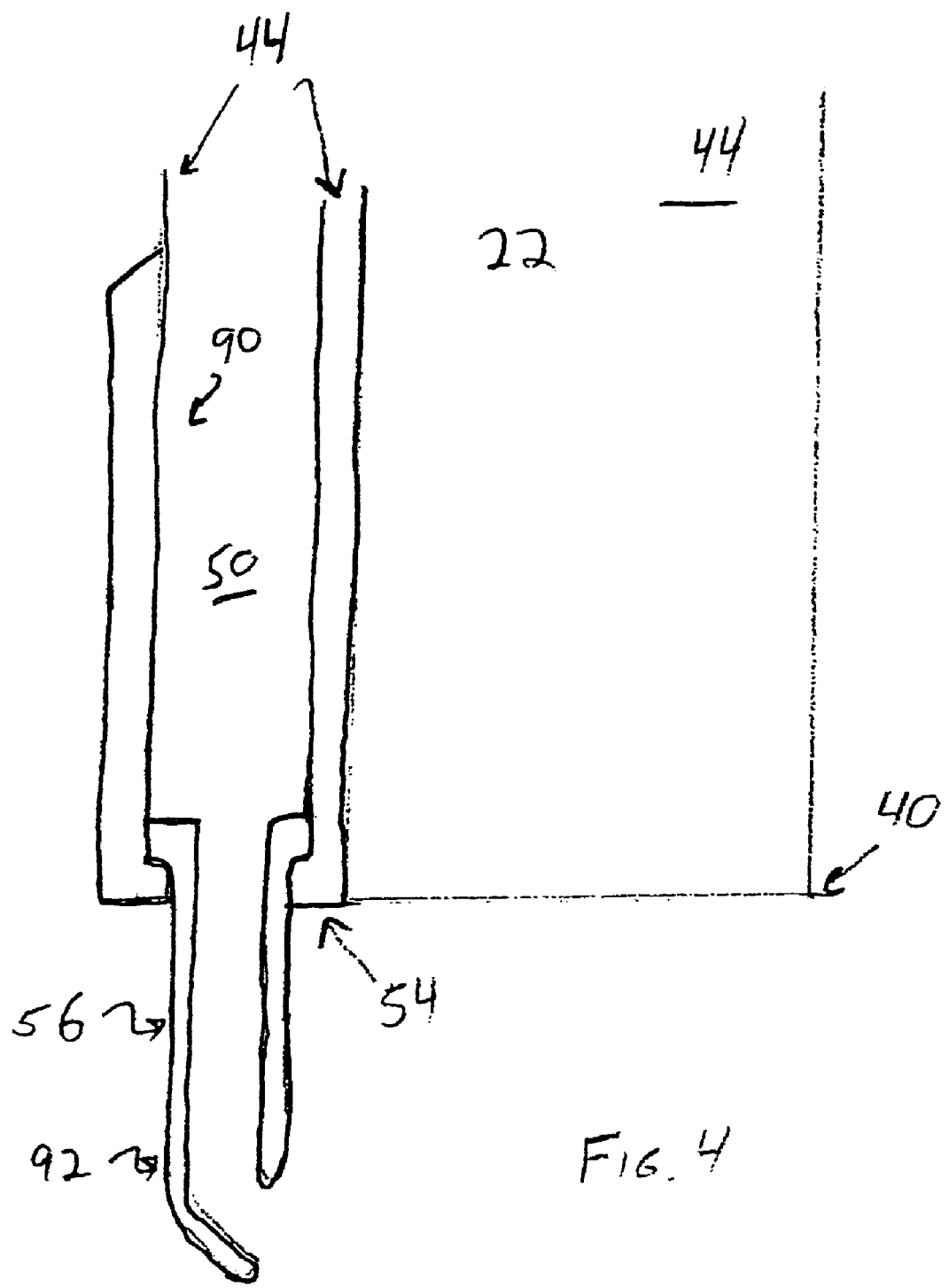
FIG. 4 is a cross-section representation of the distal end of one embodiment of the trocar tube, showing the trocar tube channel telescoping tip.

FIG. 4 illustrates a cross-section of the distal end 40 of trocar tube 20, and the operation of telescoping tip 56. Trocar tube channel distal end 54 is fitted with a flange, receiving a flange on the proximal end of trocar tube channel telescoping tip to prevent telescoping tip 56 from escaping trocar tube channel 50. Telescoping tip control 90, contained within trocar tube channel 50, is used to control the extent to which telescoping tip 56 extends from trocar tube channel distal end 54. Telescoping tip control 90 may be a wire mechanically linked to telescoping tip 90, or a pneumatic feed to an inflatable telescoping tip 90, or other control device. Telescoping tip diverter 92 directs the flow of irrigation or aspiration. Directional control or irrigation and aspiration may also be obtained through openings along the body of trocar tube channel telescoping tip 56.

The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. An apparatus comprising:
   a trocar comprising an elongated tubular member having an inner wall and an outer wall, a proximal end and a distal end;
   a suction channel along a length of said trocar between said inner wall and said outer wall;
   an irrigation channel along a length of said trocar between said inner wall and said outer wall;
   a telescoping tip connected to a distal end of said suction channel, said telescoping tip having a channel therein through which suction may be performed; and
   a flange at a distal end of said suction channel and a flange at a proximal end of said telescoping tip connected to said suction channel.

2. An apparatus according to claim 1 further comprising a telescoping tip connected to a distal end of said irrigation channel.

3. An apparatus according to claim 1 further comprising means for controlling said telescoping distal end of said suction channel.

4. An apparatus comprising:
   a trocar comprising an elongated tubular member having an inner wall and an outer wall, a proximal end and a distal end;
   a suction channel along a length of said trocar between said inner wall and said outer wall;
   an irrigation channel along a length of said trocar between said inner wall and said outer wall;
   a telescoping tip connected to a distal end of said irrigation channel, said telescoping tip having a channel therein through which irrigation may be performed; and
   a flange at a distal end of said irrigation channel and a flange at a proximal end of said telescoping tip connected to said irrigation channel.

* * * * *